(12) United States Patent
Bastian et al.

(10) Patent No.: US 11,641,890 B2
(45) Date of Patent: May 9, 2023

(54) WEARER PHYSICAL STATUS INDICATION USING AN ELECTRONICALLY ADJUSTABLE GARMENT

(71) Applicant: Kyndryl, Inc., New York, NY (US)

(72) Inventors: David Bastian, Addison, IL (US); Aaron K. Baughman, Cary, NC (US); Shikhar Kwatra, Durham, NC (US); Todd Russell Whitman, Bethany, CT (US)

(73) Assignee: KYNDRYL, INC., New York, NY (US)

( * ) Notice: Subject to any disclaimer, the term of this patent is extended or adjusted under 35 U.S.C. 154(b) by 533 days.

(21) Appl. No.: 16/778,561

(22) Filed: Jan. 31, 2020

(65) Prior Publication Data

US 2021/0235779 A1    Aug. 5, 2021

(51) Int. Cl.
| | |
|---|---|
| A41D 1/00 | (2018.01) |
| A41D 15/00 | (2006.01) |
| G06T 19/00 | (2011.01) |
| G06F 1/16 | (2006.01) |
| G06F 3/01 | (2006.01) |

(52) U.S. Cl.
CPC ........... *A41D 1/002* (2013.01); *A41D 15/002* (2013.01); *G06F 1/163* (2013.01); *G06F 3/011* (2013.01); *G06T 19/006* (2013.01)

(58) Field of Classification Search
CPC .... A41D 1/002; A41D 15/002; A61B 5/1118; A61B 5/7275; A61B 5/7445; A61B 5/7455; A61B 2503/10; A61B 2560/0242; G06F 1/163; G06F 3/011; G06F 13/00; G06F 3/165; G06T 19/006; G16H 20/30; G16H 40/63; G16H 50/30; H04W 4/021; H04W 4/023
See application file for complete search history.

(56) References Cited

U.S. PATENT DOCUMENTS

| | | |
|---|---|---|
| 8,933,889 B2 | 1/2015 | Heikkinen et al. |
| 9,763,571 B2 | 9/2017 | Kozloski et al. |
| 9,836,927 B2 | 12/2017 | Ashoori et al. |
| 10,292,651 B2 | 5/2019 | Kozloski et al. |
| 2016/0026253 A1 | 1/2016 | Bradski et al. |

(Continued)

FOREIGN PATENT DOCUMENTS

CN    101828785 B    7/2012

OTHER PUBLICATIONS

Berzowska, "Electronic Textiles: Wearable Computers, Reactive Fashion, and Soft Computation," Textile: The Journal of Cloth and Culture, vol. 3, issue 1, pp. 58-75, 2005.

(Continued)

*Primary Examiner* — Nelson M Rosario
(74) *Attorney, Agent, or Firm* — Dan Housley; Andrew M. Calderon; Calderon Safran & Cole, P.C.

(57) ABSTRACT

From a first sensor in a set of sensors, a set of sensor measurements corresponding to a wearer of a garment is collected. Using a model and the set of sensor measurements, a performance deviation index corresponding to the wearer is determined, the performance deviation index corresponding to a deviation from a baseline performance level of the wearer. Responsive to the performance deviation index being above a threshold, a characteristic of the garment is altered.

20 Claims, 10 Drawing Sheets

(56) References Cited

U.S. PATENT DOCUMENTS

| | | |
|---|---|---|
| 2016/0098860 A1 | 4/2016 | Basra |
| 2016/0335398 A1 | 11/2016 | Kozloski et al. |
| 2017/0323485 A1 | 11/2017 | Samec et al. |
| 2018/0271180 A1 | 9/2018 | Kim et al. |
| 2019/0183430 A1* | 6/2019 | Alphonse ............. A61B 5/4875 |
| 2020/0375506 A1* | 12/2020 | Bishop ................ A41C 3/0028 |
| 2021/0007874 A1* | 1/2021 | Galiana Bujanda .... A61F 5/028 |
| 2021/0195732 A1* | 6/2021 | Longinotti-Buitoni ...................... D06M 15/564 |

OTHER PUBLICATIONS

Anonymous, "System and method for Providing Visualization of Body Muscle Utilization with Electronic Ink.", IP.com Disclosure No. IPCOM000255472D, Publication Date: Sep. 27, 2018.

Fonseca, Look: NBA unveils wild new digital jersey, NJ.com, Feb. 15, 2019, https://www.nj.com/sports/2019/02/nba-announces-jersey-of-future-ahead-of-all-star-weekend.html.

* cited by examiner

WEARER PHYSICAL STATUS INDICATION USING AN ELECTRONICALLY ADJUSTABLE GARMENT

TECHNICAL FIELD

The present invention relates generally to a method, system, and computer program product for determining and electronically displaying status information. More particularly, the present invention relates to a method, system, and computer program product for wearer physical status indication using an electronically adjustable garment.

BACKGROUND

The Internet of Things (IoT) is a system of interrelated computing devices that have unique identifiers and the ability to transfer data over a network without requiring human-to-human or human-to-computer interaction. IoT devices are configurable to include one or more sensors, for example a still or video camera, microphone, wind speed sensor, temperature sensor, heart rate measurement sensor, sweat measurement sensor, accelerometer, pressure sensor, and the like. Some IoT devices can be integrated into wearable clothing, by using conductive fabric or by attaching conventional systems to conventional fabric. For example, pressure sensors integrated into socks can be used to count steps taken, as well as cadence and foot landing technique. As another example, sensors integrated into shirts can be used to monitor heart rate, respiration rate, and other forms of physical activity. IoT devices are also configurable to include an output mechanism, for example a speaker or electronic display.

Electronic ink is a substance that responds to electrical signals to enable changeable text and image displays on a flexible surface. In one electronic ink implementation, each display pixel is made from one or more capsules containing differently-colored electrophoretic particles that respond to electronic signals differently, thus causing the display pixel's color to change. The capsules can be implemented on a plastic film and the film applied to a wearable garment. Using such a display connected to an IoT device, a user can upload a design to the device for display on the garment. For example, a user can implement a custom t-shirt design by uploading a design to a t-shirt equipped with a communications device and suitable display panel.

Another electronic ink implementation integrates electronic ink directly into a fabric, by incorporating wires into individual fabric threads. An electric current flows through the wires, raising the thread's temperature sufficiently to enable special pigments embedded in the thread to respond by changing color. Applying different currents to different fabric areas allows for pattern displays. Other electronic ink implementations for use in fabric and other wearable materials are also possible.

A garment is a wearable item. Garments are often made at least partially of textile, leather, or fabric, although this is not required. Although humans typically wear garments, such as shirts, pants, and shoes, animals can also wear garments. For example, dogs often wear collars or harnesses, and horses' legs are often wrapped in fabric bandage-like boots for support or protection during exercise.

Conductive threads, and devices integrated into garments, can also be used to adjust garment properties other than color. Garment threads can be caused to lengthen or shorten, modifying the fit of a garment or a portion of the garment. Garment threads can be caused to vibrate. For example, an electronically adjustable knee brace might be tightened for additional support, or vibrate in a particular pattern to create a massage effect. Garment threads can be caused to heat up, thus heating the wearer in cold weather. Other garment adjustments are also possible.

Augmented reality (AR) is a technology that superimposes a computer generated image on a user's view of the real world, thus providing a composite view. An AR display or AR device is a device used to display AR to a user. Some examples of AR devices are AR glasses that project a computer generated image onto the glasses in the user's field of view, and smartphones that integrate the computer generated image with a camera's display of the real world.

SUMMARY

The illustrative embodiments provide a method, system, and computer program product. An embodiment includes a method that collects, from a first sensor in a set of sensors, a set of sensor measurements corresponding to a wearer of a garment. An embodiment determines, using a model and the set of sensor measurements, a performance deviation index corresponding to the wearer, the performance deviation index corresponding to a deviation from a baseline performance level of the wearer. An embodiment alters, responsive to the performance deviation index being above a threshold, a characteristic of the garment.

An embodiment includes a computer usable program product. The computer usable program product includes one or more computer-readable storage devices, and program instructions stored on at least one of the one or more storage devices.

An embodiment includes a computer system. The computer system includes one or more processors, one or more computer-readable memories, and one or more computer-readable storage devices, and program instructions stored on at least one of the one or more storage devices for execution by at least one of the one or more processors via at least one of the one or more memories.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Figure 1:
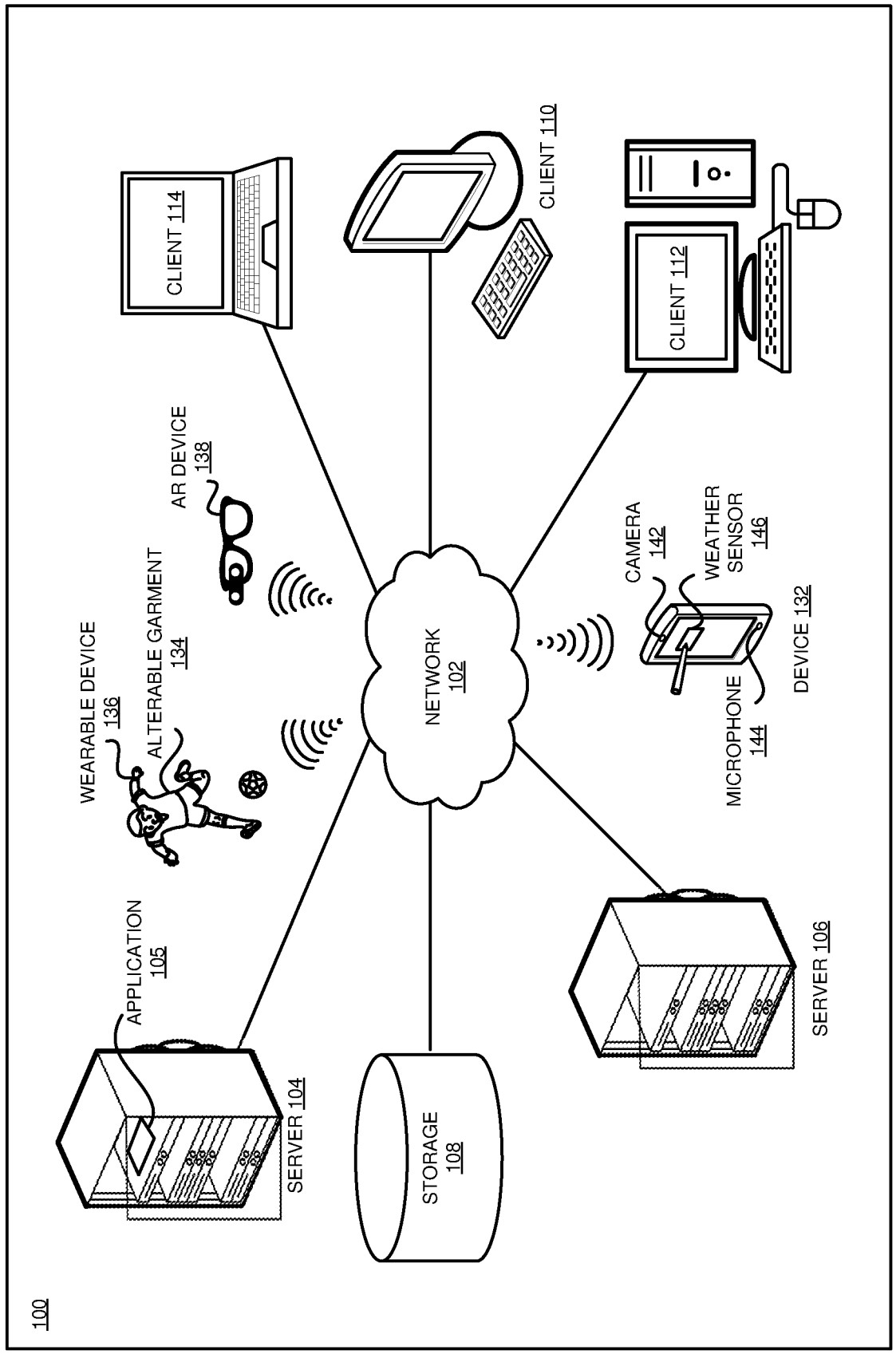
FIG. 1 depicts a block diagram of a network of data processing systems in which illustrative embodiments may be implemented.

The illustrative embodiments recognize that detecting and indicating a garment wearer's physical status can be important, but the wearer may be unaware of or ignoring his or her physical status. For example, people who are overly fatigued often perform physical tasks poorly, such as playing a sport, driving, or working in a potentially dangerous environment. Both people and domestic animals who continue a task when too fatigued to perform well are also at a higher risk of injury. However, people who are overly fatigued often ignore or do not recognize their fatigue, and those responsible for animals may not recognize fatigue either. Without such recognition it becomes difficult to ameliorate the situation. As another example, physical signs of an imminent injury may be present but go undetected until the injury actually occurs or worsens. For example, a warmer-than-normal area on a person's body may indicate a mild repetitive stress injury or an imminent tendon sprain. If undetected or not ameliorated, the mild repetitive stress injury could become more severe, or additional stress could turn the imminent sprain into an actual sprain.

The illustrative embodiments also recognize that a method used to recognize an individual's physical status should not contribute to making that status worse. For example, a heavy monitoring instrument could contribute to an individual's fatigue or, by hampering the individual's movements, contribute to the possibility of an injury.

The illustrative embodiments also recognize that a method used to indicate an individual's physical status should include a means to communicate status information only to selected others. For example, if an overly fatigued player is playing a sport, the opposing team could take advantage of the fatigued player by involving him or her in more plays, thereby worsening the player's fatigue. Thus, the illustrative embodiments recognize that there is an unmet need to recognize an individual's physical status, determine when that status has diverged beyond a threshold amount from the individual's normal state, and indicate that divergence, without worsening the individual's physical status.

The illustrative embodiments recognize that the presently available tools or solutions do not address these needs or provide adequate solutions for these needs. The illustrative embodiments used to describe the invention generally address and solve the above-described problems and other problems related to wearer physical status indication using an electronically adjustable garment.

An embodiment can be implemented as a software application. The application implementing an embodiment can be configured as a modification of an existing physical status indication system, as a separate application that operates in conjunction with an existing physical status indication system, a standalone application, or some combination thereof.

Particularly, some illustrative embodiments provide a method that collects a set of sensor measurements corresponding to a garment wearer, uses a model and the sensor measurements to determine a fatigue index corresponding to the wearer, and, if the fatigue index is above a threshold value, altering a characteristic of the garment.

An embodiment collects a set of sensor measurements from a sensor. In one embodiment, the garment wearer wears the sensor. For example, a heart rate monitor might be attached to a chest strap or wrist band, a microphone might be attached to a shirt, a temperature sensor might be integrated into a pair of pants, and a pressure sensor might be integrated into a pair of socks. In another embodiment, a system user does not wear the sensor, and the sensor is located so as to monitor the environment around the wearer. For example, a temperature, wind speed, barometer, or humidity sensor might be mounted on a soccer stadium so as to monitor weather conditions for the players in the stadium. A camera located outside the area of play might be used to observe the status of players' faces, movements of players on both teams (if a team sport is being played), the crowd's actions (e.g. standing or sitting), or weather conditions in the players' general area. Both the garment wearer and a system user who is monitored using another method opt in to participating in monitoring.

An embodiment uses sensor measurements, from one or more sensors, as inputs to a model. An embodiment also uses additional data, for example from a database or other data repository, as inputs to the model. The additional data relates to an individual's biographic information and the state of the individual's current activity. Some non-limiting examples of an individual's biographic information are how many years of experience and how much recent experience the individual has, as well as past injury data. If the individual is playing baseball, for example, the state of the individual's current activity might include the inning number, how many outs there are, and which bases any runners are on. If the individual is playing soccer, for example, the state of the individual's current activity might include the current score, and the current minute of play. If the individual is playing golf, for example, the state of the individual's current activity might include which round of a tournament is currently being played, the player's total number of strokes in the tournament, and the hole number as well as data about the length, shape, and terrain of the hole. If the individual is welding, for example, the current state of the individual's activity might include the number of hours the individual has already worked in the current day and work week, as well as a measure of the complexity of the individual's current welding task. In addition, if the individual is playing a spectator sport, for example, the state of the individual's current activity might include spectator status information, such as the audience's level of cheering as determined by analyzing the words in an audience's utterances, whether a portion of the audience is standing rather than sitting, and the audience's noise level.

Some input variables in the model (e.g., weather data) are measured directly. Other input variables (e.g. which hole the golfer is currently playing) are obtained from a statistics module, database, or other data repository. Other input variables (e.g. whether or not the audience is cheering, a player's excitement level and expression, the player's stride length and gait evenness) are the results of an analysis of one or more types of sensor data. For example, whether or not the audience is cheering might be the result of analyzing words spoken by members of the audience using data collected using a microphone, analyzing whether a portion of the audience is standing rather than sitting using data collected using a camera, and measuring the audience's noise level using a decibel meter.

The model outputs a performance deviation index for an individual, corresponding to the individual's deviation from a baseline performance level. In one embodiment, the baseline performance level corresponds to the individual. In another embodiment, the baseline performance level corresponds to a group with similar characteristics to the individual. In another embodiment, the baseline performance level is not specific to an individual or group. In one embodiment, the performance deviation index corresponds to an individual's fatigue level, and the baseline performance level corresponds to a baseline fatigue level. In another embodiment, the performance deviation index does not correspond to a fatigue level, but does reflect other indications that an individual is not performing as usual. For example, signs of an imminent injury may manifest as a gait irregularity or a skin region that is warmer than usual.

In one embodiment, the model is a decision tree. A decision tree is a construct in which each node represents an attribute, each branch represents a decision, and each leaf represents a result. For example, a one-node decision tree might include one node, representing wind speed being greater than thirty miles per hour. The left branch from this node represents a path taken if the wind speed is greater than thirty miles per hour, leading to an outcome that it is too windy to play baseball. The right branch from this node represents a path taken if the wind speed is not greater than thirty miles per hour, leading to an outcome that it is not too windy to play baseball.

An embodiment uses a set of training data to construct the model. The training data includes sensor measurement data, additional data, or a combination of both. One presently-available technique for constructing a decision tree begins by determining the attribute that best classifies the training data and uses this attribute at the root of the tree, then repeating the attribute determination at each branch below the root until the data has been sufficiently classified, the tree depth reaches a predefined limit, or another stopping point is reached. To determine the best attribute at each level, one presently-available technique is to compute a Gini impurity, a measure of how often a randomly chosen element from the training set would be incorrectly labeled if the element was randomly labeled according to the distribution of labels in the training set. Other presently-available techniques to determine the best attribute at each level, to construct a decision tree using another technique, and to model training data using a technique other than a decision tree are also possible and contemplated within the scope of the illustrative embodiments.

One non-limiting example of a set of training data, for use in evaluating a performance deviation index corresponding to a golfer's fatigue level, includes whether or not the audience is cheering, a player's excitement level and expression, how many years of experience a player has, how many of a player's parents and grandparents played golf or any sport, the player's hole, tournament round, and stroke number, hole data such as the par number and yardage, how many times the player has hit a terrain feature while playing a hole, the number of attempts a player required to complete playing a hole, wind speed, temperature, humidity, barometric pressure, the player's heart rate and sweat level, and the player's stride length and gait evenness while walking between holes.

Using the constructed model and input data including sensor measurements corresponding to an individual, an embodiment determines a performance deviation index corresponding to the individual. If the model is a decision tree, an embodiment uses the model by beginning at the top of the decision tree and following branches according to the input data until arriving at a leaf. For example, a decision tree model configured to determine a performance deviation index corresponding to a soccer player might follow branches for the player's heart rate being above a threshold heart rate, the ambient temperature and humidity being above thresholds, the ambient wind speed being below a threshold, and the player's gait being classified as uneven to determine that the player has a performance deviation index above a threshold.

If the individual's performance deviation index is above a threshold, an embodiment uses a set of rules to determine a strategy adjustment corresponding to the individual. The set of rules includes, for example, a rule that if an individual's performance deviation index is above a threshold, alter a characteristic of a garment worn by the individual. In embodiments, the altered characteristic is an alteration in a color, pattern, or other visible garment characteristic. For example, the individual's shirt might be changed from his or her team uniform color to red, or a shirt area changed from a solid-color area to an area with diagonal stripes. Using a visible garment characteristic indicates to others, for example a worker's manager or a player's teammates and coaches, that the individual's status has changed, allowing others to ameliorate the situation, perhaps by resting the worker or substituting a different player. In other embodiments, the altered characteristic is an alteration in a fiber length of one or more fibers in the garment, rendering a portion of the garment tighter or looser than a starting state. For example, a waist portion of a pair of pants might be tightened and loosened, or vibrated, to privately indicate to the wearer to take action to ameliorate his or her situation, perhaps by resting. In other embodiments, the altered characteristic is an alteration in a characteristic displayable using an augmented reality application. For example, when viewed using an augmented reality application, the individual's shirt might appear as a different color, as blinking in a pattern, or otherwise highlighted. Displaying the alteration using an augmented reality application allows for keeping the individual's status private, for example visible only to a player's coach, so that an opposing team cannot take advantage of the individual's changed status.

The set of rules includes, for example, one or more strategy adjustments to be implemented if an individual's performance deviation index is above a threshold. One example strategy adjustment is to encourage spectators to support the individual whose garment characteristic has been visibly altered, to help the individual overcome fatigue. Another example strategy adjustment is to alter a garment characteristic so as to ameliorate the wearer's situation. For example, if an individual's performance deviation index indicates an imminent knee injury, the individual's knee wrap could be tightened to provide additional support and prevent a more serious injury.

An embodiment uses further input data corresponding to an individual as input to the model, to determine if an individual's performance deviation index remains above a threshold or returns to a baseline or intermediate value. If the individual's performance deviation index is no longer above a threshold, one embodiment returns a garment characteristic to its original state.

An embodiment uses further input data corresponding to an individual after a strategy adjustment to determine a result of the strategy adjustment. An embodiment uses strategy adjustment results to improve the set of rules governing strategy adjustments and any specific adjustments. For example, if encouraging spectators to support a fatigued individual results in the individual's performance deviation index returning to a baseline level, an embodiment considered this to be a successful strategy adjustment suitable for use on other home team players, and will be more likely to apply this adjustment to others. However, as another example, if tightening an individual's knee wrap has no effect on the individual's performance deviation index, an embodiment considered this to be an unsuccessful strategy adjustment, and will be less likely to apply this adjustment in the future.

The manner of wearer physical status indication using an electronically adjustable garment described herein is unavailable in the presently available methods in the technological field of endeavor pertaining to status detection and indication. A method of an embodiment described herein, when implemented to execute on a device or data processing system, comprises substantial advancement of the functionality of that device or data processing system in collecting a set of sensor measurements corresponding to a garment wearer, using a model and the sensor measurements to determine a fatigue index corresponding to the wearer, and, if the fatigue index is above a threshold value, altering a characteristic of the garment.

The illustrative embodiments are described with respect to certain types of garments, garment characteristics, types of data, thresholds, responses, adjustments, sensors, measurements, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific code, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 2:
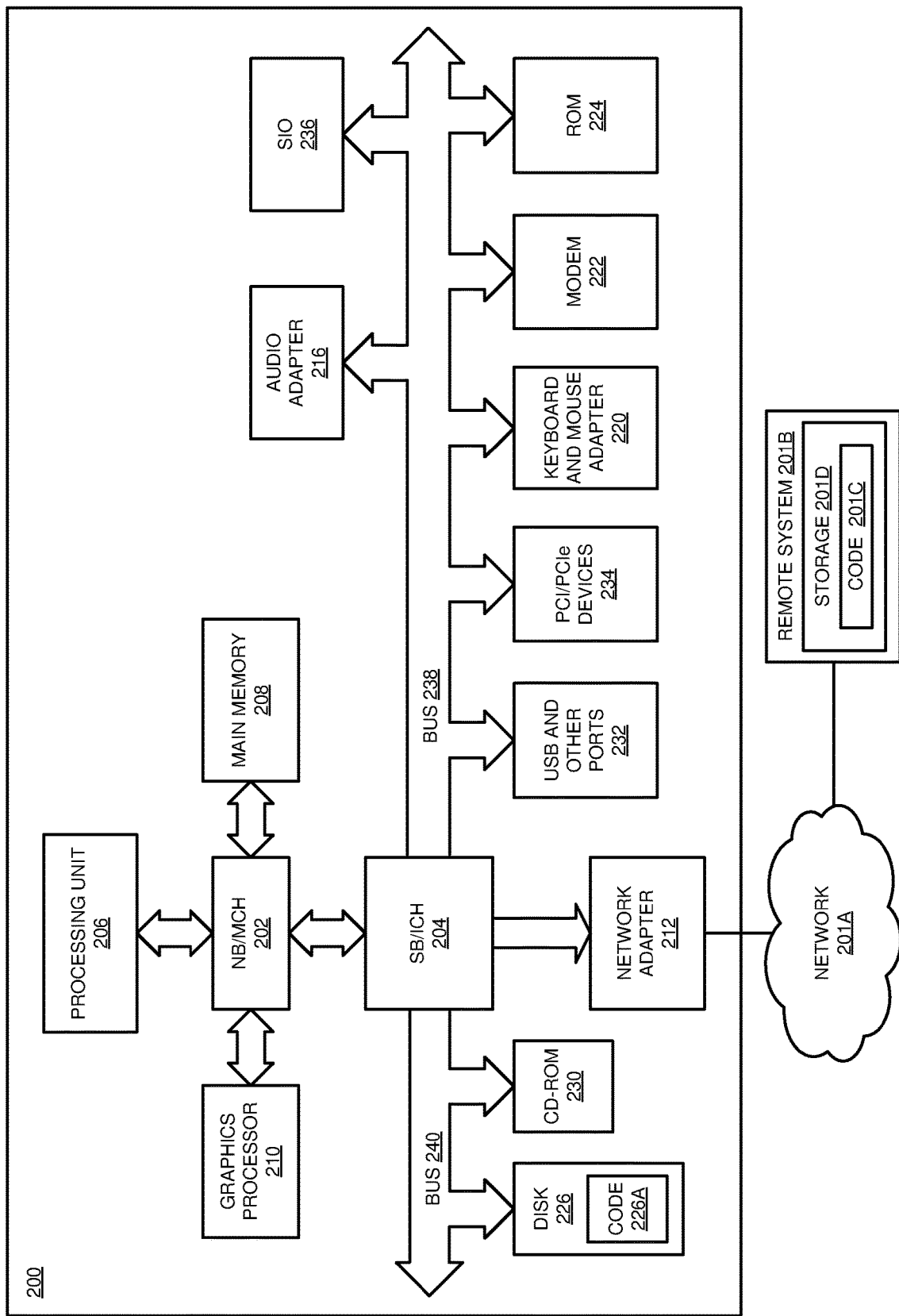
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Server 104 and server 106 couple to network 102 along with storage unit 108. Software applications may execute on any computer in data processing environment 100. Clients 110, 112, and 114 are also coupled to network 102. A data processing system, such as server 104 or 106, or client 110, 112, or 114 may contain data and may have software applications or software tools executing thereon.

Only as an example, and without implying any limitation to such architecture, FIG. 1 depicts certain components that are usable in an example implementation of an embodiment. For example, servers 104 and 106, and clients 110, 112, 114, are depicted as servers and clients only as example and not to imply a limitation to a client-server architecture. As another example, an embodiment can be distributed across several data processing systems and a data network as shown, whereas another embodiment can be implemented on a single data processing system within the scope of the illustrative embodiments. Data processing systems 104, 106, 110, 112, and 114 also represent example nodes in a cluster, partitions, and other configurations suitable for implementing an embodiment.

Device 132 is an example of a device described herein. Device 132 includes camera 142, microphone 144, and weather sensor 146. For example, device 132 can take the form of a smartphone, a tablet computer, a laptop computer, client 110 in a stationary or a portable form, a wearable computing device, or any other suitable device. Any software application described as executing in another data processing system in FIG. 1 can be configured to execute in device 132 in a similar manner. Any data or information stored or produced in another data processing system in FIG. 1 can be configured to be stored or produced in device 132 in a similar manner.

Alterable garment 134, wearable device 136, and AR device 138 are examples of a device described herein. Alterable garment 134 is capable of altering a garment characteristic in response to receiving a signal, for example via network 102. Wearable device 136 is capable of measuring sensor measurement data and sending data, for example via network 102. AR device 138 is capable of displaying an output of an AR application to a viewer. Any software application described as executing in another data processing system in FIG. 1 can be configured to execute in alterable garment 134, wearable device 136, and AR device 138 in a similar manner. Any data or information stored or produced in another data processing system in FIG. 1 can be configured to be stored or produced in alterable garment 134, wearable device 136, and AR device 138 in a similar manner.

Application 105 implements an embodiment described herein. Application 105 executes in any of servers 104 and 106, clients 110, 112, and 114, and device 132. Application 105 receives sensor data input from camera 142, microphone 144, weather sensor 146, and wearable device 136, and produces output via alterable garment 134 and AR device 136 as well as servers 104 and 106, clients 110, 112, and 114, and device 132.

Servers 104 and 106, storage unit 108, clients 110, 112, and 114, and devices 132, 134, 136, and 138 may couple to network 102 using wired connections, wireless communication protocols, or other suitable data connectivity. Clients 110, 112, and 114 may be, for example, personal computers or network computers.

In the depicted example, server 104 may provide data, such as boot files, operating system images, and applications to clients 110, 112, and 114. Clients 110, 112, and 114 may be clients to server 104 in this example. Clients 110, 112, 114, or some combination thereof, may include their own data, boot files, operating system images, and applications. Data processing environment 100 may include additional servers, clients, and other devices that are not shown.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such as servers 104 and 106, or clients 110, 112, and 114 in FIG. 1, or another type of device in which computer usable program code or instructions implementing the processes may be located for the illustrative embodiments.

Data processing system 200 is also representative of a data processing system or a configuration therein, such as data processing system 132 in FIG. 1 in which computer usable program code or instructions implementing the processes of the illustrative embodiments may be located. Data processing system 200 is described as a computer only as an example, without being limited thereto. Implementations in the form of other devices, such as device 132 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to NB/MCH 202 through an accelerated graphics port (AGP) in certain implementations.

In the depicted example, local area network (LAN) adapter 212 is coupled to South Bridge and I/O controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and I/O controller hub 204 through bus 238. Hard disk drive (HDD) or solid-state drive (SSD) 226 and CD-ROM 230 are coupled to South Bridge and I/O controller hub 204 through bus 240. PCI/PCIe devices 234 may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and I/O controller hub (SB/ICH) 204 through bus 238.

Memories, such as main memory 208, ROM 224, or flash memory (not shown), are some examples of computer usable storage devices. Hard disk drive or solid state drive 226, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 105 in FIG. 1, are located on storage devices, such as in the form of code 226A on hard disk drive 226, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory 224, or in one or more peripheral devices.

Furthermore, in one case, code 226A may be downloaded over network 201A from remote system 201B, where similar code 201C is stored on a storage device 201D. in another case, code 226A may be downloaded over network 201A to remote system 201B, where downloaded code 201C is stored on a storage device 201D.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub 202. A processing unit may include one or more processors or CPUs.

The depicted examples in FIGS. 1-2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and disk 226 is manifested as a virtualized instance of all or some portion of disk 226 that may be available in the host data processing system. The host data processing system in such cases is represented by data processing system 200.

Figure 3:
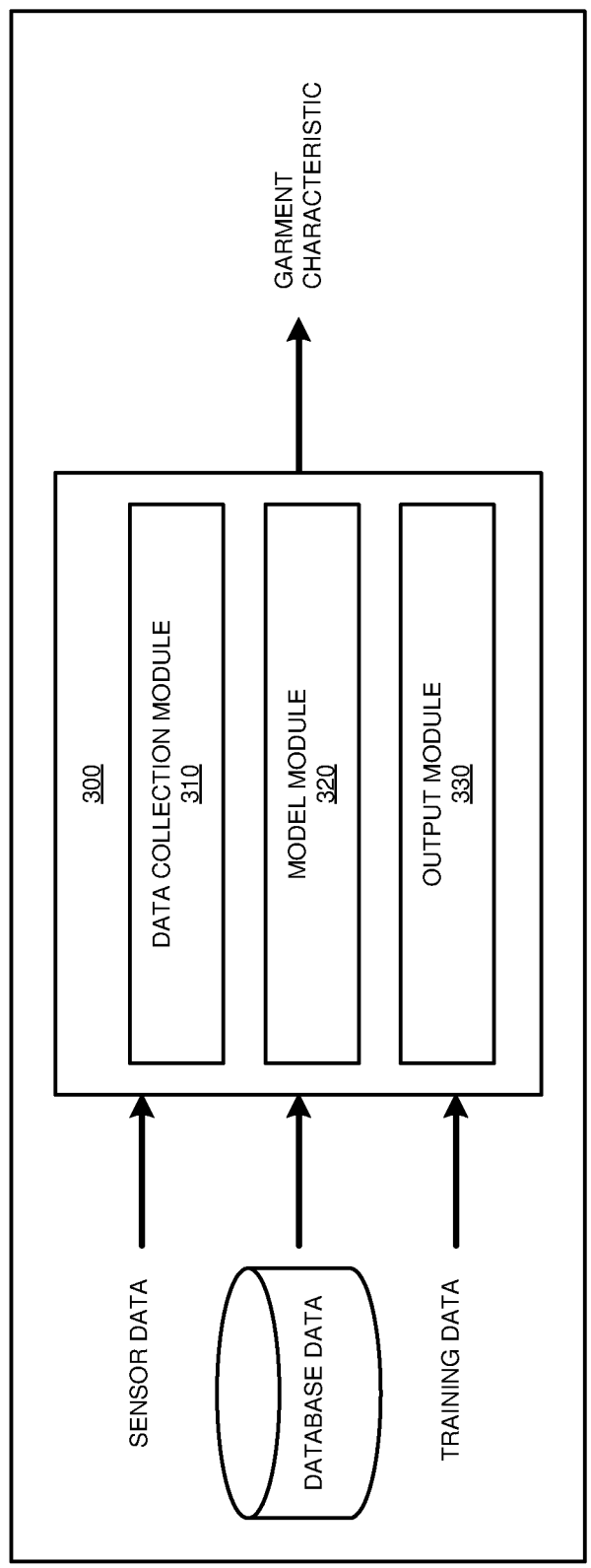
FIG. 3 depicts a block diagram of an example configuration for wearer physical status indication using an electronically adjustable garment in accordance with an illustrative embodiment.

With reference to FIG. 3, this figure depicts a block diagram of an example configuration for wearer physical status indication using an electronically adjustable garment in accordance with an illustrative embodiment. Application 300 is an example of application 105 in FIG. 1 and executes in any of servers 104 and 106, clients 110, 112, and 114, and device 132 in FIG. 1.

Data collection module 310 collects sensor measurement data, data from a database, and training data, for use as input variables to a model. Some input variables in the model (e.g., weather data) are measured directly. Other input variables (e.g. which hole the golfer is currently playing) are obtained from a statistics module, database, or other data repository. Other input variables (e.g. whether or not the audience is cheering, a player's excitement level and expression, the player's stride length and gait evenness) are the results of an analysis of one or more types of sensor data. For example, whether or not the audience is cheering might be the result of analyzing words spoken by members of the audience using data collected using a microphone, analyzing whether a portion of the audience is standing rather than sitting using data collected using a camera, and measuring the audience's noise level using a decibel meter.

Model module 320 outputs a performance deviation index for an individual or group, corresponding to a deviation from a baseline performance level. In one implementation, module 320 implements the performance deviation index using a decision tree. If the individual's performance deviation index is above a threshold, module 320 uses a set of rules to determine a strategy adjustment corresponding to the individual. Output module 330 alter a characteristic of a garment worn by the individual, such as a human-visible or AR-visible characteristic or an alteration in a fiber length of one or more fibers in the garment, rendering a portion of the garment tighter or looser than a starting state. More detail of modules 310, 320, and 330 is provided with reference to FIGS. 4, 5, and 6.

Figure 4:
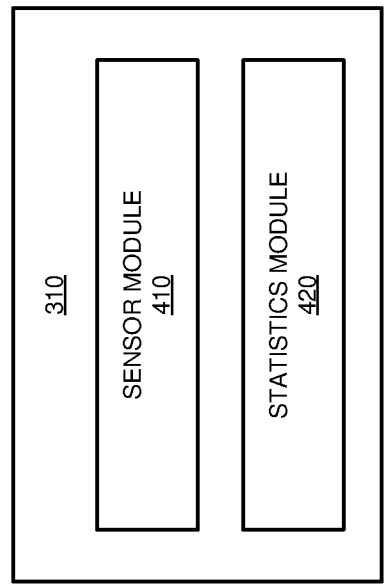
FIG. 4 depicts a block diagram of an example configuration for wearer physical status indication using an electronically adjustable garment in accordance with an illustrative embodiment.

With reference to FIG. 4, this figure depicts a block diagram of an example configuration for wearer physical status indication using an electronically adjustable garment in accordance with an illustrative embodiment. Module 310 is the same as module 310 in FIG. 3.

Within data collection module 310, sensor module 410 collects a set of sensor measurements from a sensor. The sensor can be worn by a garment wearer or located so as to monitor the environment around the wearer. Statistics module 420 collects and manages additional data relating to an individual's biographic information and the state of the individual's current activity.

Figure 5:
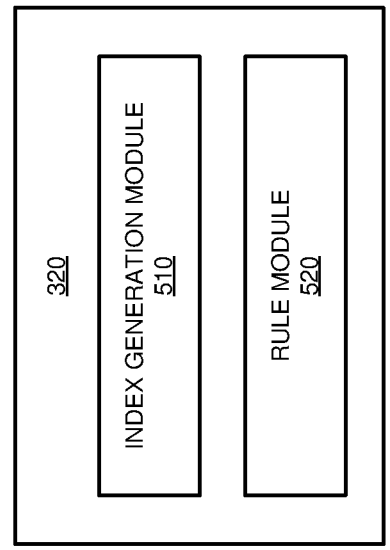
FIG. 5 depicts a block diagram of an example configuration for wearer physical status indication using an electronically adjustable garment in accordance with an illustrative embodiment.

With reference to FIG. 5, this figure depicts a block diagram of an example configuration for wearer physical status indication using an electronically adjustable garment in accordance with an illustrative embodiment. Module 320 is the same as module 320 in FIG. 3.

Within model module 320, index generation module 510 outputs a performance deviation index for an individual, corresponding to the individual's deviation from a baseline performance level. In one implementation, the baseline performance level corresponds to the individual. In another implementation, the baseline performance level corresponds to a group with similar characteristics to the individual. In another implementation, the baseline performance level is not specific to an individual or group. In one implementation, the performance deviation index corresponds to an individual's fatigue level, and the baseline performance level corresponds to a baseline fatigue level. In another implementation, the performance deviation index does not correspond to a fatigue level, but does reflect other indications that an individual is not performing as usual. For example, signs of an imminent injury may manifest as a gait irregularity or a skin region that is warmer than usual. In one implementation, module 510 implements a decision tree.

Module 510 uses a set of training data to construct the model. The training data includes sensor measurement data, additional data, or a combination of both. Using the constructed model and input data including sensor measurements corresponding to an individual, module 510 determines a performance deviation index corresponding to the individual.

Rule module 520 manages a set of rules to determine a strategy adjustment corresponding to the individual. Rule module 520 also uses further input data corresponding to an individual after a strategy adjustment to determine a result of the strategy adjustment. Module 520 uses strategy adjustment results to improve the set of rules governing strategy adjustments and any specific adjustments.

Figure 6:
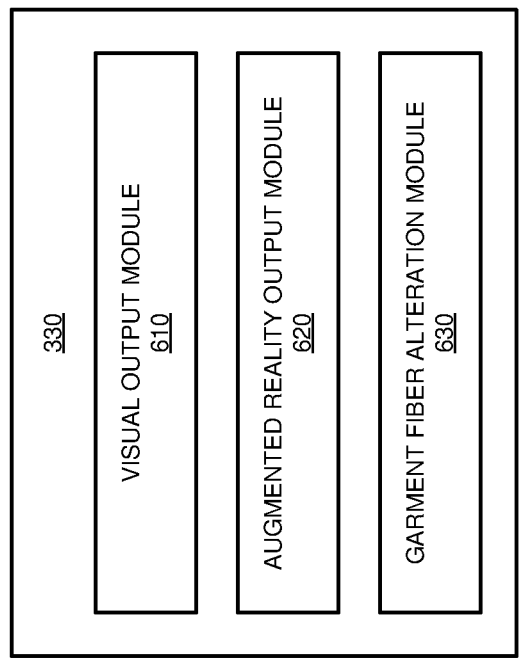
FIG. 6 depicts a block diagram of an example configuration for wearer physical status indication using an electronically adjustable garment in accordance with an illustrative embodiment.

With reference to FIG. 6, this figure depicts a block diagram of an example configuration for wearer physical status indication using an electronically adjustable garment in accordance with an illustrative embodiment. Module 330 is the same as module 330 in FIG. 3.

Within output module 330, visual output module 610 alters a garment's color, pattern, or other visible garment characteristic. For example, the individual's shirt might be changed from his or her team uniform color to red, or a shirt area changed from a solid-color area to an area with diagonal stripes. Augmented reality output module 620 alters a garment characteristic displayable using an augmented reality application. For example, when viewed using an augmented reality application, the individual's shirt might appear as a different color, as blinking in a pattern, or otherwise highlighted. Garment fiber alteration module 630 alters a fiber length of one or more fibers in the garment, rendering a portion of the garment tighter or looser than a starting state. For example, a waist portion of a pair of pants might be tightened and loosened, or vibrated, to privately indicate to the wearer to take action to ameliorate his or her situation, perhaps by resting.

Figure 7:
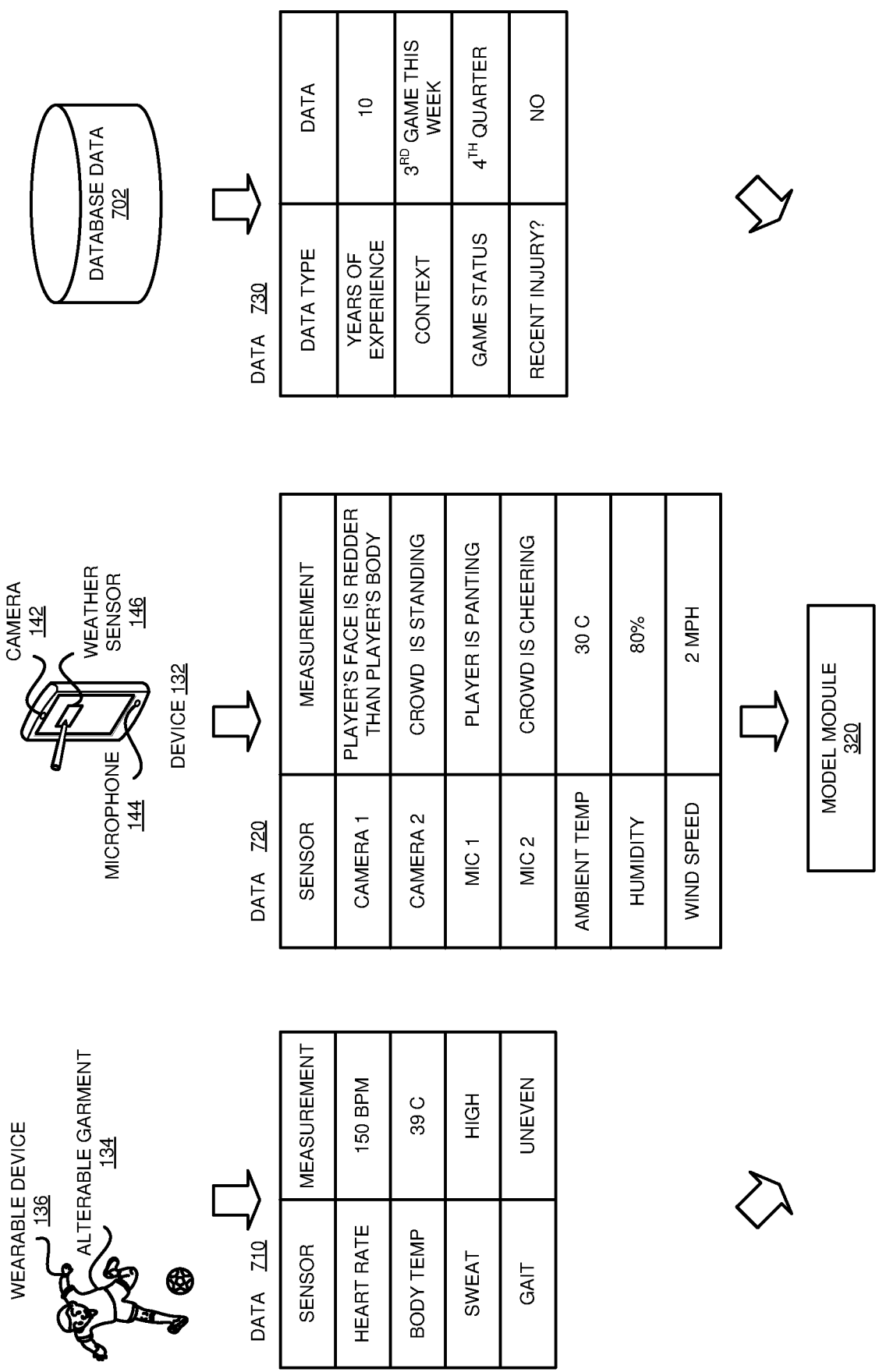
FIG. 7 depicts an example of wearer physical status indication using an electronically adjustable garment in accordance with an illustrative embodiment.

With reference to FIG. 7, this figure depicts an example of wearer physical status indication using an electronically adjustable garment in accordance with an illustrative embodiment. The example can be executed using application 300 in FIG. 3. Alterable garment 134, wearable device 136, device 132, camera 142, microphone 144, and weather sensor 146 are the same as alterable garment 134, wearable device 136, device 132, camera 142, microphone 144, and weather sensor 146 in FIG. 1. Model module 320 is the same as model module 320 in FIG. 3.

As depicted, one or more of wearable device 136 produce sensor data 710 relating to an individual. Camera 142, microphone 144, and weather sensor 146 produce sensor data 720, relating to an environment around the individual. Database data 702 includes data 730, relating to the individual's biographic information and the state of his or her current activity. Each of data 710, 720, and 730 is input to model module 320. The example data depicted in data 710, 720, and 730 is intended only as a non-limiting example of data inputs to model module 320.

Figure 8:
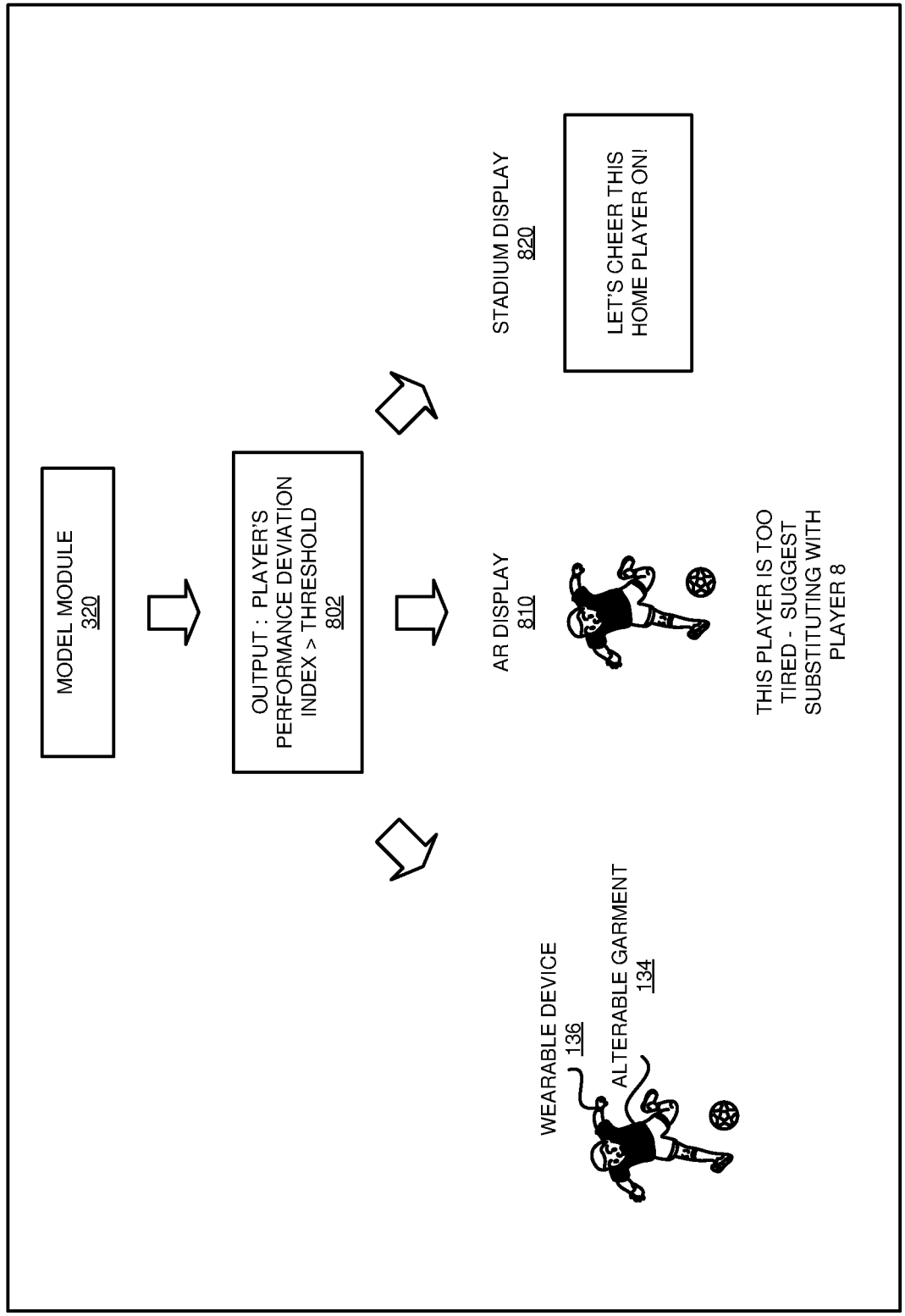
FIG. 8 depicts a continued example of wearer physical status indication using an electronically adjustable garment in accordance with an illustrative embodiment.

With reference to FIG. 8, this figure depicts a continued example of wearer physical status indication using an electronically adjustable garment in accordance with an illustrative embodiment. Alterable garment 134, wearable device 136, and model module 320 are the same as alterable garment 134, wearable device 136, and model module 320 in FIG. 7.

As depicted, model module 320 has produced output 802: this player's performance deviation index is above a threshold, indicating that this player has become overly fatigued. As one result, application 300 changes the color of alterable garment 134 from its previous white to black. As another result, application 300 alters a characteristic of the player's shirt, so that the player is displayed using AR display 810, with a notation indicating that this player is too tired and suggesting substituting with player B. As a third result, application 300 displays a message on stadium display 820, asking spectators to cheer for the tired player.

Figure 9:
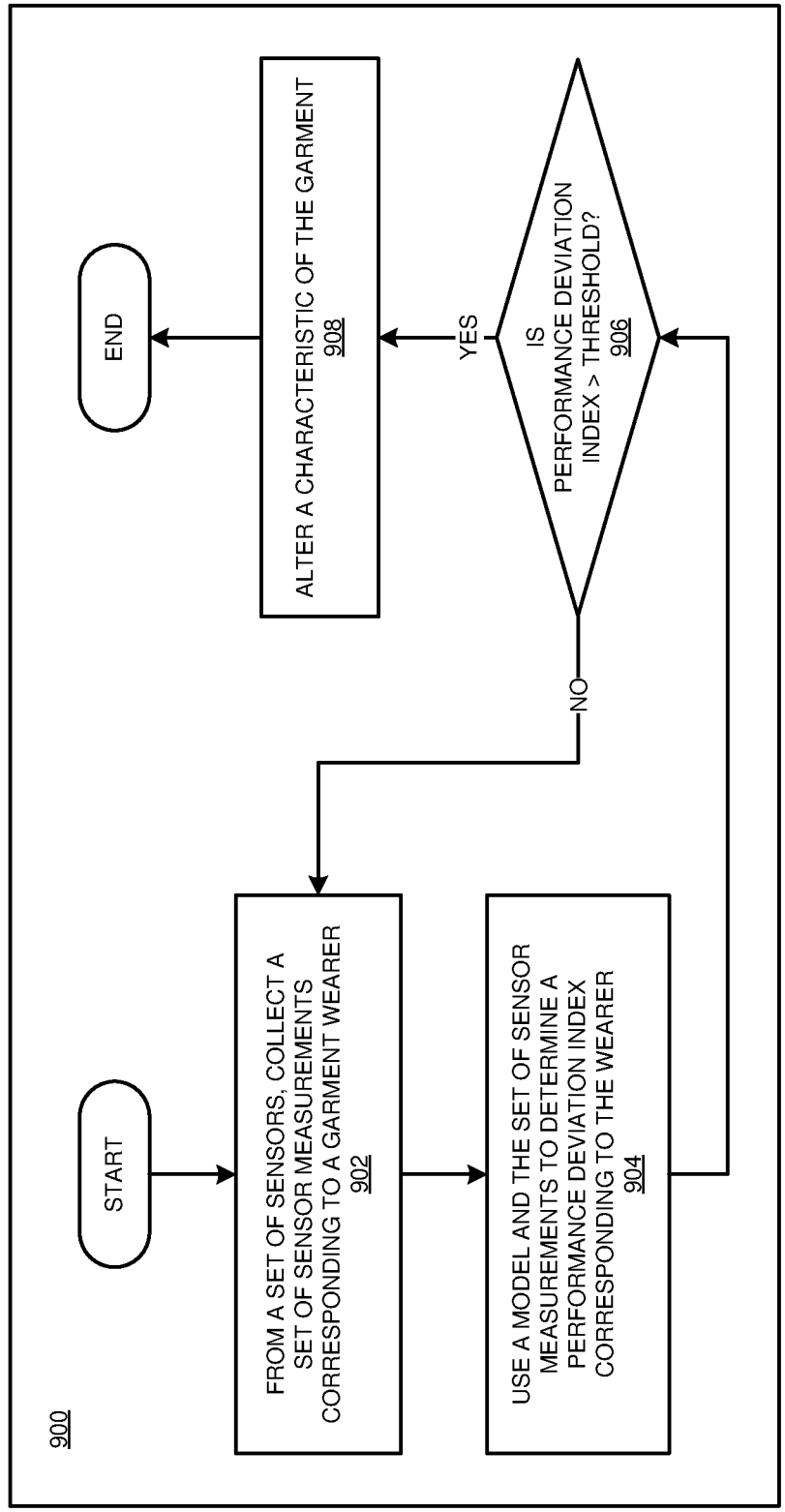
FIG. 9 depicts a flowchart of an example process for wearer physical status indication using an electronically adjustable garment in accordance with an illustrative embodiment.

With reference to FIG. 9, this figure depicts a flowchart of an example process for wearer physical status indication using an electronically adjustable garment in accordance with an illustrative embodiment. Process 900 can be implemented in application 300 in FIG. 3.

In block 902, the application, from a set of sensors, collects a set of sensor measurements corresponding to a garment wearer. In block 904, the application uses a model and the set of sensor measurements to determine a performance deviation index corresponding to the wearer. In block 906, the application checks whether the performance deviation index is greater than a threshold. If not ("NO" path of block 906), the application returns to block 902 to continue collecting measurements. Otherwise ("YES" path of block 906), in block 908, the application alters a characteristic of the garment. Then the application ends.

Figure 10:
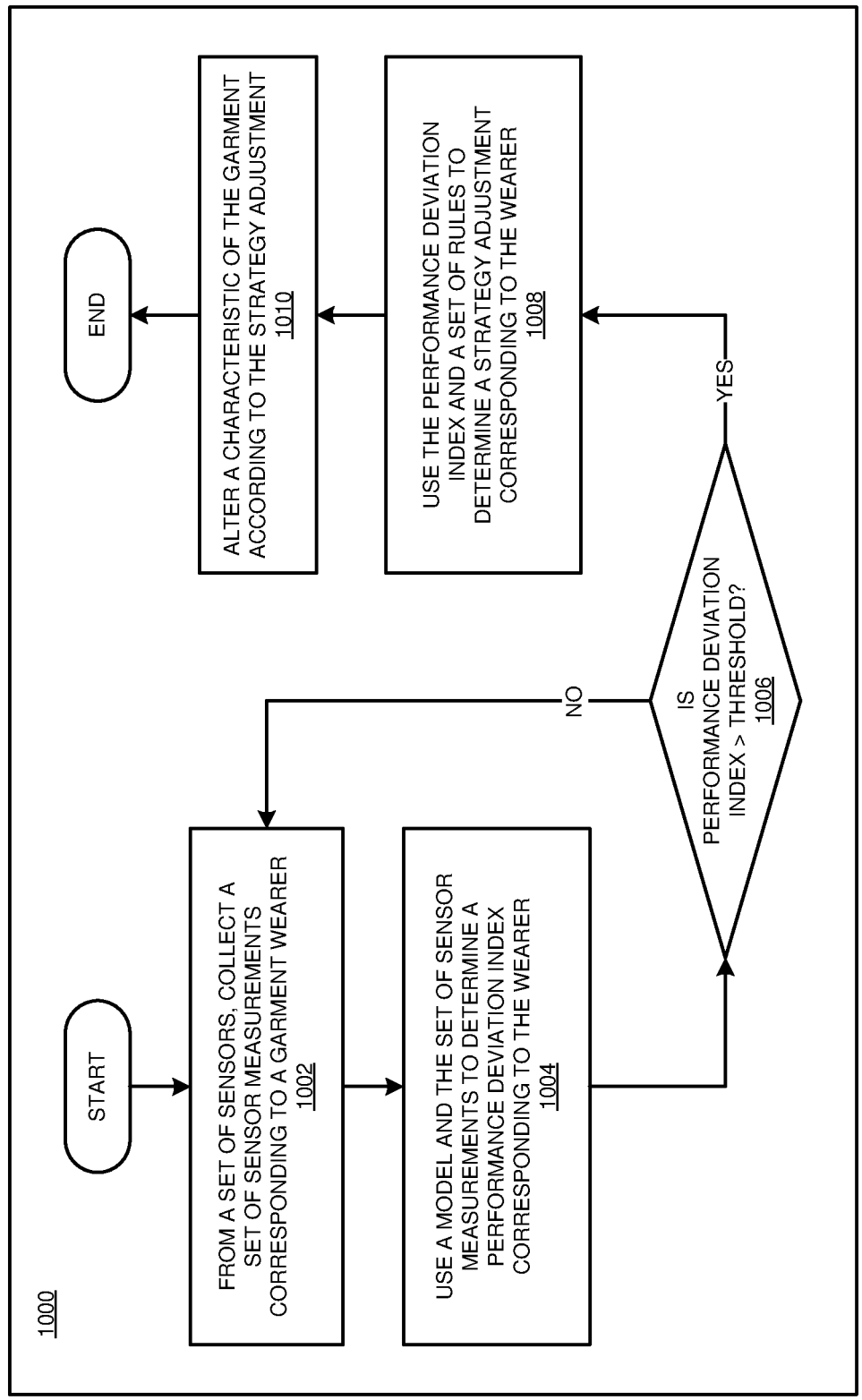
FIG. 10 depicts a flowchart of an example process for wearer physical status indication using an electronically adjustable garment in accordance with an illustrative embodiment.

With reference to FIG. 10, this figure depicts a flowchart of an example process for wearer physical status indication using an electronically adjustable garment in accordance with an illustrative embodiment. Process 1000 can be implemented in application 300 in FIG. 3.

In block 1002, the application, from a set of sensors, collects a set of sensor measurements corresponding to a garment wearer. In block 1004, the application uses a model and the set of sensor measurements to determine a performance deviation index corresponding to the wearer. In block 1006, the application checks whether the performance deviation index is greater than a threshold. If not ("NO" path of block 1006), the application returns to block 1002 to continue collecting measurements. Otherwise ("YES" path of block 1006), in block 1008, the application uses the performance deviation index and a set of rules to determine a strategy adjustment corresponding to the wearer. In block 1010, the application alters a characteristic of the garment according to the strategy adjustment. Then the application ends.

Thus, a computer implemented method, system or apparatus, and computer program product are provided in the illustrative embodiments for wearer physical status indication using an electronically adjustable garment and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method comprising:
   collecting, from a first sensor in a set of sensors, a set of sensor measurements corresponding to a wearer of a garment;
   determining, using a model and the set of sensor measurements, a performance deviation index corresponding to the wearer, the performance deviation index corresponding to a deviation from a baseline performance level of the wearer; and
   altering, responsive to the performance deviation index being above a threshold, a characteristic of the garment, wherein the model includes biographic information of the wearer received from a database, which is used to determine the performance deviation, and
   wherein the model includes a decision tree comprising a node, a branch and a leaf, in which the model is a construct such that each node represents an attribute, each branch represents a decision, and each leaf represents a result.

2. The computer-implemented method of claim 1, further comprising:
   determining, using the performance deviation index and a set of rules, a strategy adjustment corresponding to the wearer; and
   altering, according to the strategy adjustment, the characteristic of the garment.

3. The computer-implemented method of claim 2, further comprising:
   collecting, from the first sensor subsequent to the strategy adjustment, a second set of sensor measurements corresponding to the wearer;
   determining, using the model and the second set of sensor measurements, a second performance deviation index corresponding to the wearer; and
   adjusting, using the second performance deviation index, the set of rules.

4. The computer-implemented method of claim 1, wherein the first sensor comprises a wearable sensor and further input variables including weather data and data unrelated to a physical status of the wearer is provided in the model.

5. The computer-implemented method of claim 1, wherein altering a characteristic of the garment comprises altering a visual characteristic of the garment.

6. The computer-implemented method of claim 5, wherein altering a characteristic of the garment comprises altering a characteristic displayable using an augmented reality application executing in a computer system, the computer system comprising a display and further comprising:
   training to construct the model using training data, the training data including sensor measurement data and additional data, the training comprising constructing the decision tree by determining an attribute that best classifies the training data and using the attribute at the root of the decision tree, then repeating the attribute determination at each branch below the root until the training data has been classified, a depth of the decision tree reaches a predefined limit, or a stopping point is reached, wherein to determine the best attribute comprises a measure of how often a randomly chosen element from the training data would be incorrectly labeled if the element was randomly labeled according to distribution of labels in the training data.

7. The computer-implemented method of claim 1, wherein altering a characteristic of the garment comprises altering a fiber length of a fiber of the garment.

8. A computer usable program product comprising one or more computer-readable storage medium, and program instructions stored on at least one of the one or more storage medium, the stored program instructions comprising:
   program instructions to collect, from a first sensor in a set of sensors, a set of sensor measurements corresponding to a wearer of a garment;
   program instructions to determine, using a model and the set of sensor measurements, a performance deviation index corresponding to the wearer, the performance deviation index corresponding to a deviation from a baseline performance level of the wearer; and
   program instructions to alter, responsive to the performance deviation index being above a threshold, a characteristic of the garment,
   wherein the model includes biographic information of the wearer received from a database, which is used to determine the performance deviation, and
   wherein the model includes a decision tree comprising a node, a branch and a leaf, in which the model is a construct such that each node represents an attribute, each branch represents a decision, and each leaf represents a result.

9. The computer usable program product of claim 8, further comprising:
   program instructions to determine, using the performance deviation index and a set of rules, a strategy adjustment corresponding to the wearer; and
   program instructions to alter, according to the strategy adjustment, the characteristic of the garment.

10. The computer usable program product of claim 9, further comprising:
    program instructions to collect, from the first sensor subsequent to the strategy adjustment, a second set of sensor measurements corresponding to the wearer;
    program instructions to determine, using the model and the second set of sensor measurements, a second performance deviation index corresponding to the wearer; and
    program instructions to adjust, using the second performance deviation index, the set of rules.

11. The computer usable program product of claim 8, wherein the first sensor comprises a wearable sensor and further input variables including weather data and data unrelated to a physical status of the wearer is provided in the model.

12. The computer usable program product of claim 8, wherein program instructions to alter a characteristic of the garment comprises program instructions to alter a visual characteristic of the garment.

13. The computer usable program product of claim 8, wherein program instructions to alter a characteristic of the garment comprises program instructions to alter a characteristic displayable using an augmented reality application executing in a computer system, the computer system comprising a display.

14. The computer usable program product of claim 8, wherein program instructions to alter a characteristic of the garment comprises program instructions to alter a fiber length of a fiber of the garment.

15. The computer usable program product of claim 8, wherein the stored program instructions are stored in the at least one of the one or more storage devices of a local data processing system, and wherein the stored program instructions are transferred over a network from a remote data processing system.

16. The computer usable program product of claim 8, wherein the stored program instructions are stored in the at least one of the one or more storage devices of a server data processing system, and wherein the stored program instructions are downloaded over a network to a remote data processing system for use in a computer readable storage device associated with the remote data processing system.

17. A computer system comprising one or more processors, one or more computer-readable memories, and one or more computer-readable storage devices, and program instructions stored on at least one of the one or more storage devices for execution by at least one of the one or more processors via at least one of the one or more memories, the stored program instructions comprising:

program instructions to collect, from a first sensor in a set of sensors, a set of sensor measurements corresponding to a wearer of a garment;

program instructions to determine, using a model and the set of sensor measurements, a performance deviation index corresponding to the wearer, the performance deviation index corresponding to a deviation from a baseline performance level of the wearer; and program instructions to alter, responsive to the performance deviation index being above a threshold, a characteristic of the garment, wherein the model includes biographic information of the wearer received from a database, which is used to determine the performance deviation, and wherein the model includes a decision tree comprising a node, a branch and a leaf, in which the model is a construct such that each node represents an attribute, each branch represents a decision, and each leaf represents a result.

18. The computer system of claim 17, further comprising:

program instructions to determine, using the performance deviation index and a set of rules, a strategy adjustment corresponding to the wearer; and program instructions to alter, according to the strategy adjustment, the characteristic of the garment.

19. The computer system of claim 18, further comprising:

program instructions to collect, from the first sensor subsequent to the strategy adjustment, a second set of sensor measurements corresponding to the wearer;

program instructions to determine, using the model and the second set of sensor measurements, a second performance deviation index corresponding to the wearer; and program instructions to adjust, using the second performance deviation index, the set of rules.

20. The computer system of claim 17, wherein the first sensor comprises a wearable sensor and further input variables including weather data and data unrelated to a physical status of the wearer is provided in the model.

\* \* \* \* \*